(12) United States Patent
Monaghan et al.

(10) Patent No.: US 6,916,816 B2
(45) Date of Patent: Jul. 12, 2005

(54) PHENANTHRYL PIPERAZINYL DICARBOXYLIC ACIDS AS SELECTIVE NMDA RECEPTOR MODULATING AGENTS

(75) Inventors: Daniel T. Monaghan, Omaha, NE (US); David E. Jane, Bristol (GB); Heong Wai Tse, Bristol (GB)

(73) Assignees: The Board of Regents of the University of Nebraska, Lincoln, NE (US); The University of Bristol, Bristol (GB)

( * ) Notice: Subject to any disclaimer, the term of this patent is extended or adjusted under 35 U.S.C. 154(b) by 204 days.

(21) Appl. No.: 10/149,847

(22) PCT Filed: Dec. 18, 2000

(86) PCT No.: PCT/US00/34137
§ 371 (c)(1),
(2), (4) Date: Sep. 3, 2002

(87) PCT Pub. No.: WO01/44205
PCT Pub. Date: Jun. 21, 2001

(65) Prior Publication Data
US 2003/0078237 A1 Apr. 24, 2003

(30) Foreign Application Priority Data
Dec. 16, 1999 (GB) .............................................. 9929582

(51) Int. Cl.[7] .................. A61K 31/497; A61K 31/4965
(52) U.S. Cl. ............................ 514/252.12; 514/255.01; 514/255.02; 514/255.03; 514/255.06; 544/380; 544/391
(58) Field of Search ................... 514/255.06, 255.01, 514/255.02, 255.03, 252.12; 544/391, 380

(56) References Cited

U.S. PATENT DOCUMENTS 5,595,983 A * 1/1997 Watkins et al. ............... 514/85
5,985,586 A 11/1999 Daggett et al.

FOREIGN PATENT DOCUMENTS

EP 0 159 889 A2 10/1985

OTHER PUBLICATIONS

Buller, A.L. et al. "Pharmacological heterogeneity of NMDA receptors: characterization of NR1 a/NR2D heteromers expressed in *Xenopus* oocytes"; European Journal of Pharmacology, 320: 87–94 (1997).

Hrabetova, S. et al. "Distinct NMDA Receptor Subpopulations Contribute to Long–Term Potentiation and Long–Term Depression Induction"; The Journal of Neuroscience, 20: 1–6 (2000).

* cited by examiner

*Primary Examiner*—Peter G. O'Sullivan
(74) *Attorney, Agent, or Firm*—Dann, Dorfman, Herrell & Skillman, P.C.

(57) ABSTRACT

Disclosed are compounds of formula (I) wherein: L is (a) optionally substituted by replacement of one or more of the hydrogen atoms on the phenanthrene ring system by one or more groups other than hydrogen; A is $CH_2$, $SO_2$ or $C=O$; X is $CO_2H$, $PO_3H_2$, $PO_2H_2$, $PO_2HR^5$, $PO_2HOR^5$, $SO_3H$, $SO_2H$, or tetrazole; and $R^1$, $R^2$, $R^3$, $R^4$ and $R^5$ are independently selected from H, alkyl, alkenyl, alkynyl, aryl and aralkyl; or a pharmaceutically acceptable acid salt or base addition salt or an in vivo hydrolysable ester or amide thereof. Compounds of formula (I) are selective NMDA receptor modulating agents and, therefore, may be used to advantage in vitro in neuroassays and in vivo in the treatment of disorders of the CNS

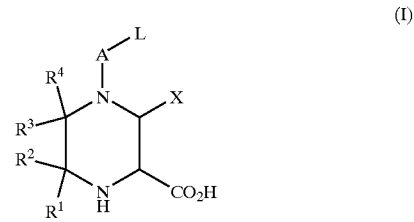

(I)

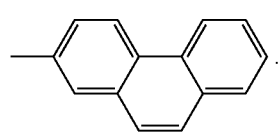

(a)

16 Claims, 1 Drawing Sheet

PHENANTHRYL PIPERAZINYL DICARBOXYLIC ACIDS AS SELECTIVE NMDA RECEPTOR MODULATING AGENTS

The present application is the U.S. National Phase of PCT/US00/34137, filed Dec. 18, 2000.

Pursuant to 35 U.S.C. §202(c) it is hereby acknowledged that this invention was made with government support under DAMD-17-94-C-4050, awarded by the Department of the Army. The Government has certain rights in this invention.

FIELD OF THE INVENTION

This invention relates to phenanthryl piperazinyl dicarboxylic acids (PPDAs), processes for synthesizing the same and methods of use thereof in vivo and in vitro.

BACKGROUND OF THE INVENTION

NMDA receptors consist of NMDA receptor 1 (NR1) subunits and members of a family of glutamate-binding NR2 subunits (NR2A-D) (Ikeda K, et al. (1992) FEBS Lett 313:34–38; Monyer H, et al. (1992) Science 256:1217–1221; Ishii T, et al. (1993) J Biol Chem 268:2836–2843). Recombinant NMDA receptors that contain NR1 subunits and subunits NR2A or B require a strong depolarization to overcome $Mg^{2+}$ blockade and have high conductances, whereas those with NR2C or D need only modest depolarization to overcome $Mg^{2+}$ blockade and show low conductances (Monyer et al., id., and Monyer H, et al. (1994) Neuron 12:529–540). Native NMDA receptors containing NR2D are estimated to form ~10% of the NMDA receptor population in the cortex of adult rats (Dunah A W, et al. (1998) Mol Pharmacol 53:429–437). Additionally, levels of expression of these subunits are higher in juvenile animals Dunah A W, et al. (1996) J Neurochem 67:2335–2345; Wenzel A, et al. (1996) J Neurochem 66:1240–1248), in which long-term depression can most efficiently be produced (Dudek S M, Bear M F (1993) J Neurosci 13:2910–2918.). CA1 pyramidal cells express mRNA for NR2A, 2B, and 2D in adult humans (Scherzer C R, et al. (1998) J Comp Neurol 390:75–90) and in juvenile rats (Kirson ED, et al. (1999) J Physiol (Lond) 521:99–111). Currents attributable to NMDA receptors containing NR2D subunits have also been observed in juvenile CA1 pyramidal cells (Kirson et al., id.).

NMDA receptor subpopulations containing these different subunits can be distinguished by competitive NMDA receptor antagonists with different affinities to the glutamate-binding site of the various NR2s (Monaghan D T, et al. (1998) Prog Brain Res 116:158–177).

In the hippocampal CA1 region and the cerebral cortex, both long-term potentiation (LTP) and long-term depression (LTD) can depend on the activation of NMDA receptors, because both can be blocked by the NMDA receptor antagonist D/L-2-amino-5- phosphonovaleric acid (D/L-AP5) (Collingridge G L, et al. (1983) J Physiol (Lond) 334:34–46; Harris E W, et al. (1984) Brain Res 323:132–137; Dudek S M, Bear M F (1992) Proc Natl Acad Sci USA 89:4363–4367; Mulkey R M, Malenka R C (1992) Neuron 9:967–975; Kirkwood A, et al. (1993) Science 260:1518–1521; Christie B R, et al. (1996) Learn Mem 3:160–169; Cummings J A, et al. (1996) Neuron 16:825–833). High-frequency stimulation causes strong activation of the ligand- and voltage-dependent NMDA receptors. A large influx of $Ca^{2+}$ into postsynaptic neurons follows to trigger potentiation. Low-frequency stimulation results in moderate activation of NMDA receptors and a moderate influx of $Ca^{2+}$, leading to depression. An additional mechanism participating in this bi-directional response, however, may be that high- and low-frequency stimulation activate distinct subpopulations of NMDA receptors (Hrabetova S, Sacktor T C (1997) Neurosci Lett 226:107–110).

Various amino acids have become of interest following the discovery that they are able to influence the binding and modulation of certain receptors in the central nervous system (CNS), including the NMDA receptor. Attention has been directed to the identification of novel compounds that selectively bind and activate or block these receptor sites. Such compounds may be used to advantage to treat disorders resulting from CNS malfunction including, for example, various involuntary muscular activity and/or mental and/or affective disorders.

A number of piperazine-2-carboxylic acid and piperazine-2,3-dicarboxylic acid analogues have been synthesised as potential NMDA receptor antagonists. EP-A-0159889 and GB-A-2157685 disclose several such compounds, including 1-(4-bromobenzoyl)-piperazine-2,3-dicarboxylic acid (BrBzPDA). The compounds are, however, relatively weak NMDA receptor antagonists and they are also relatively non-selective for the NMDA receptors, in that they also antagonize alpha-amino-3-hydroxy-5-methylisoxazole-4-propionic acid (AMPA) and kainate-induced depolarizations on neonatal rat motoneurones.

A more potent and selective NMDA receptor antagonist, namely 1-(4-phenylbenzoyl)-piperazine-2,3-dicarboxylic acid, (PBPD), has been described by Buller et al., European Journal of Pharmacology, 320, (1997), 87–94. PBPD displays some NMDA receptor subtype selectivity. Indeed, PBPD displays the opposite selectivity to previously described antagonists such as 4-(3-phosphonoprop-2-enyl) piperazine-2-carboxylic acid (CPP-ene) in that it selectively antagonises NR1/NR2B or NR1/NR2D receptors over those containing NR1/NR2A or NR1/NR2C. However, PBPD is only of moderate potency when compared to previously described antagonists such as CPP-ene.

There remains a need for NMDA receptor antagonists which have high potency and/or exhibit selectivity for particular NMDA receptor subtypes. It is an aim of the invention to provide such compounds

SUMMARY OF THE INVENTION

According to the present invention, there are provided compounds of formula

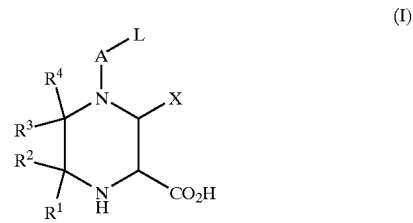

(I)

wherein: L is

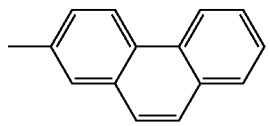

optionally substituted by replacement of one or more of the hydrogen atoms on the phenanthrene ring system by one or more groups other than hydrogen;

A is $CH_2$, $SO_2$ or C=O;

X is $CO_2H$, $PO_3H_2$, $PO_2H_2$, $PO_2HR^5$, $PO_2HOR^5$, $SO_3H$, $SO_2H$, or tetrazole; and $R^1$, $R^2$, $R^3$, $R^4$ and $R^5$ are independently selected from H, alkyl, alkenyl, alkynyl, aryl and aralkyl;

or a pharmaceutically acceptable acid salt or base addition salt or an in vivo hydrolysable ester or amide thereof.

In a further aspect of the invention, methods of synthesizing compounds of formula (I) are provided. Methods for assessing the NMDA receptor modulating activity of the compounds of formula (I) are also disclosed. In a preferred embodiment of the invention, neuroassays are utilized to assess the potency and selectivity of the compounds of the invention.

In yet another aspect of the invention, compounds of formula (I) are employed for the diagnosis and treatment of CNS disorders due to aberrant NMDA receptor activity. Also provided are pharmaceutical compositions comprising compounds of formula (I) for administration to patients in need thereof.

DETAILED DESCRIPTION OF THE INVENTION

Figure 1:
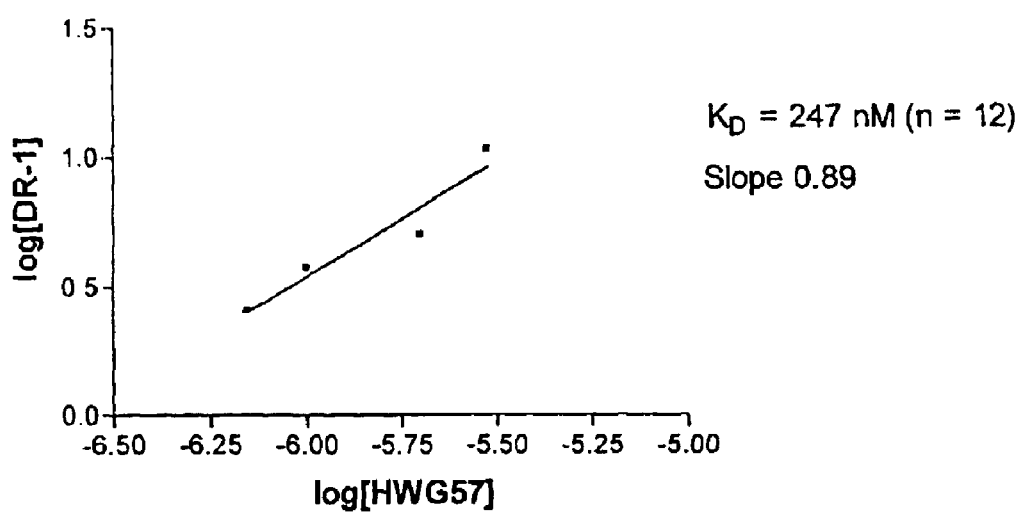
FIG. 1 is a graph showing the results of a Schild analysis of NMDA-induced depolarizations in the spinal cord. The data reveal that PPDA, also referred to herein as HWG57, is a competitive antagonist with an affinity ($K_d$) of 247 nM.

According to the present invention, there are provided compounds of formula (I)

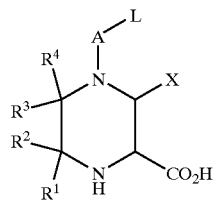

(I)

wherein: L is

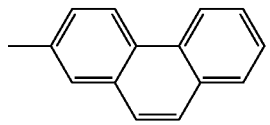

optionally substituted by replacement of one or more of the hydrogen atoms on the phenanthrene ring system by one or more groups other than hydrogen;

A is $CH_2$, $SO_2$ or C=O;

X is $CO_2H$, $PO_3H_2$, $PO_2H_2$, $PO_2HR^5$, $PO_2HOR^5$, $SO_3H$, $SO_2H$, or tetrazole; and $R^1$, $R^2$, $R^3$, $R^4$ and $R^5$ are independently selected from H, alkyl, alkenyl, alkynyl, aryl and aralkyl;

or a pharmaceutically acceptable acid salt or base addition salt or an in vivo hydrolysable ester or amide thereof.

Group L in the compounds of formula (I), which is based on a phenanthrene ring system, is optionally substituted with one or more (ie, from one to nine) groups which may be the same or different. Optional substituents on L include, for example, halo, cyano, hydroxy, alkoxy, alkyl, alkenyl, alkynyl, aryl, aralkyl, which latter five groups are all optionally substituted with one or more groups selected from halo, cyano, hydroxy, alkoxy, alkyl, alkenyl, alkynyl, aryl and aralkyl. Preferably, L is unsubstituted.

Preferably, in the compounds of formula (I), A is C=O.

Compounds of formula (I), which are also referred to herein as "compounds of the invention", comprise group X, an acidic moiety. Preferably, X is —$CO_2H$.

The term "alkyl", as used herein, includes branched and unbranched $C_1$ to $C_6$ alkyl (e.g., methyl, ethyl, 1-propyl, 2-propyl, 1-butyl and 2-(2-methylpropyl)) and $C_3$ to $C_6$ cycloalkyl (e.g., cyclopropyl, cyclobutyl, cyclopentyl and cyclohexyl). The terms "alkenyl" and "alkynyl" are defined similarly, but the groups to which they refer contain at least one carbon-carbon double bond or triple bond, respectively. "Alkoxy" means alkyl terminated with an oxygen radical (e.g., methoxy, ethoxy, propoxy, butoxy). The term "alkylene" includes $C_1$ to $C_6$ alkylene and is a diradical in which the two radical groups are separated by one or more CR'R" groups, wherein R' and R" independently represent H or alkyl.

The term "aryl", as used herein, includes aromatic, carbocylic and heterocyclic ring systems, optionally substituted on the ring by one or more further groups. Aryl thus includes phenyl, naphthyl, pyridyl, thiophenyl and furanyl, for example, all optionally substituted. Suitable substituents on the aryl ring systems include, for example, one or more of the same or different groups selected from halo, cyano, hydroxy, nitro, alkyl, alkenyl and alkynyl. "Aralkyl" means alkyl substituted with aryl e.g., benzyl.

The term "halo", as used herein, covers fluoro, chloro, bromo and iodo. "Haloalkyl" means alkyl substituted with one or more of the same or different halo groups e.g., chloromethyl or trifluoromethyl.

The compounds of the invention may be in the form of pharmaceutically acceptable acid salts or base addition salts. Suitable acid salts include, for example, sodium salts formed by deprotonation of one or more of the acidic groups (e.g., carboxylic acid groups) in the compounds of formula (I). Suitable base addition salts include, for example, salts formed between the compounds of formula (I) and an acid, such as hydrochloric acid for example, by protonation of an amino group. The compound of formula (I) may be in the form of in vivo hydrolysable esters (e.g., formed by esterification of one or more of the acidic groups in the compounds of the invention) or amides (e.g., formed by acylation of one or more of the amino groups in the compounds of the invention).

Compounds of formula (I) have one or more chiral centers and may be in the form of a racemic mixture of enantiomers, a mixture of enantiomers substantially enriched in one enantiomer or a substantially pure enantiomer. Similarly, compounds of formula (I) may be in the form of a single diastereomer or mixtures of diastereomers. It is preferred for compounds of formula (I) that groups X and —$CO_2H$, as shown in formula (I) are cis to each other on the six-membered piperazine ring.

Preferred compounds of the invention include 1-(phenanthrene-2-ylcarbonyl)piperazine-2,3-dicarboxylic acid, and, more preferably, cis-1-(phenanthrene-2-ylcarbonyl)piperazine-2,3-dicarboxylic acid.

Compounds of formula (I) may exist in one or more tautomeric forms, all of which are included in the present invention.

The compounds of the invention may be produced by a number of routes. In another aspect, the present invention provides a process for preparing the compounds which comprises the reaction of a compound of formula (II)

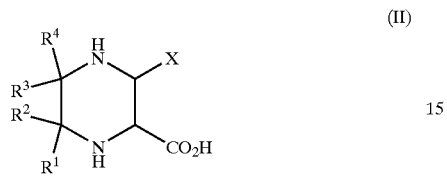

(II)

with a compound of formula L-A-M, wherein: $R^1$, $R^2$, $R^3$, $R^4$, X, L and A are as defined above for compounds of formula (I) and M is a leaving group.

The process of the invention is typically carried out in a solvent for a time and at a temperature to produce sufficient amounts of the compound of formula (I). Preferably, the process includes the steps of separating the compound of formula (I) from the reaction mixture and then purifying the compound of formula (I). The process of the invention may involve, for example, the use of a compound of formula L-A-M in which M is halo, when A is $CH_2$, $SO_2$ or CO, or in which M is —OH, —OR''' or —OC(O)OR''' (wherein R''' is alkyl, aryl or aralkyl), when A is CO. In the case in which A is CO, the process may comprise the reaction of a compound of formula (II) with an acyl halide of formula L-COCl, in a polar solvent such as 1,4-dioxane, at room temperature for 1 to 4 hours. The process may comprise the separation of the compound of formula (I) from the reaction mixture by ion exchange resin chromatography and, optionally, further purification by recrystallisation from a suitable solvent, e.g., water.

Compounds of formula (II) are commercially available or are obtainable from commercially available compounds by standard routes. For example, compounds of formula (II) in which X is $CO_2H$ may be prepared from the corresponding pyrazine compound by reduction with hydrogen in the presence of a catalyst (e.g. $PtO_2$).

In one preferred embodiment, (±)-cis-1-(10-bromophenanthrene-2-carbonyl)piperazine-2,3-dicarboxylic acid (bromoPPDA, 5) was synthesised according to Scheme 1. Phenanthrene-2-carboxylic acid (1) was brominated with bromine in acetic acid at 70° C. to give the bromo derivative (2) which was converted into the acid chloride (3) using thionyl chloride. The acid chloride (2) was coupled to (_)-cis-piperazine-2,3-dicarboxylic acid (4) in an aqueous sodium hydroxide/dioxan mixture to give the target molecule (5) which was purified by crystallization from water.

Scheme 1

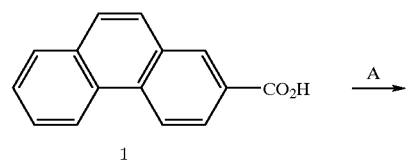

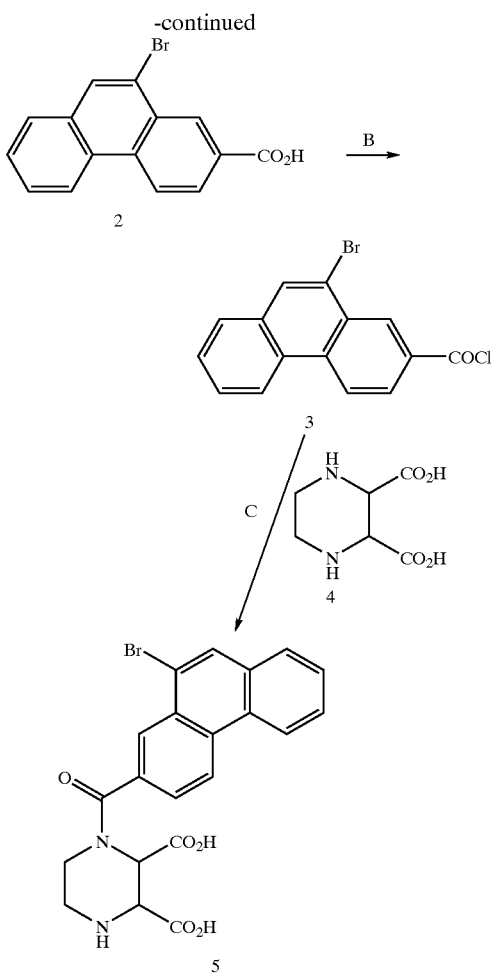

Reagents: A, Bromine, acetic acid; B, $SOCl_2$, benzene
C, NaOH (aq)/dioxan

Compounds of formula (I) possess NMDA receptor modulating activity in vitro and in vivo. As such, they may be used to advantage in the treatment of CNS disorders arising from aberrant NMDA receptor activity.

The present invention provides also provides neuroassay methods for screening and identifying test compounds which selectively bind and modulate particular NMDA receptor subtypes. This assay is also useful to determine which of the many sites of action on the NMDA receptor complex is targeted by the test compound. For example, depending on its site of action, a test compound may be a channel blocker, a glycine site agonist/antagonist, a glutamate binding site agonist/antagonist, or it may act at other known pharmacological sites on the NMDA receptor complex. Furthermore, the methods of the invention are amenable to molecular biological manipulation. The molecular mechanism of action of candidate test compounds can be confirmed by studying the effect of the test compounds on genetically altered NMDA receptor complexes in which specific amino acid residues have been modified.

An exemplary method of the invention involves incubating host cells in the presence of a test compound suspected of having NMDA receptor modulating action and assessing whether the test compound selectively binds and activates the NMDA receptor. Modulation of the NMDA receptor may be assessed in a variety of ways including, without limitation, assessing alterations in membrane depolarization, current influx, second messenger signal transduction, radioligand binding, intracellular calcium elevation, and cell death. Significantly, some of these methods (e.g. intracellular calcium measurements) are amenable to high throughput drug screening.

Another exemplary method of the invention involves incubating host cells in the presence of a compound whose ability to modulate NMDA receptors has been quantified and assessing the extent of inhibition of augmentation or attenuation of modulation in the presence of a test compound. For example, cultured transformed mammalian cells may be transformed with nucleic acids encoding specific NMDA receptor subunits and then compounds can be screened using a "flipper" assay which measures alterations in intracellular calcium in a high throughput screening assay (using 96 well, or larger, plates).

The host cells utilized in the methods of the invention may express endogenously encoding NMDA receptor subtypes, such as neonatal rat motor neuronal cells. Alternatively, cells may be genetically engineered to express recombinant NMDA receptor subtypes. Such host cells include without limitation, Xenopus oocytes, yeast cells, NIH 3T3 cells, HELA cells, and CHO cells.

In a preferred aspect of the invention, plasmids encoding NMDA receptor subtypes are linearized and transcribed in vitro. The MRNA so generated is then injected into Xenopus oocytes resulting in NMDA receptor expression in the oocyte membrane. Genetically engineered cells are then contacted with test compounds such as agonists and antagonists specific for the NMDA receptor subtypes expressed. Modulation of receptor activity is then assessed utilizing any of the methods described above.

The present invention also provides pharmaceutical compositions comprising a compound of the invention together with a pharmaceutically acceptable diluent or carrier. The pharmaceutically acceptable diluents or carriers which are suitable for use in any given composition depends upon the intended mode of administration of the composition and will be well-known to those skilled in the art.

The compounds of the invention may be administered parenterally or orally, e.g., intravenously for acute treatment, or subcutaneously, or orally for chronic treatment. Compounds of the invention may be formulated for clinical use in suitable vehicles, normally as preparations of a water-soluble salt, though preparations of low water solubility, and optionally in association with physiologically tolerable emulsifying agents.

For enhanced efficacy, it may be necessary for compounds of the invention to penetrate the blood brain barrier. In such cases, the compounds of the present invention may be administered in excess amounts to ensure that appropriate concentrations of the compounds are achieved within the brain for the therapeutic effect desired. Accordingly, this will influence the concentration of the active compounds in the compositions of the present invention. Considerations of this type indicate that compositions might contain the active compound in a concentration such that a conventional dosage volume would provide the subject with up to about 150–350 mg/kg body weight and more preferably 200 mg/kg body weight. When the compounds are to be administered by the intravenous or subcutaneous route, dosages in the region of about 1–20 mg/kg body weight are suitable for the more active compounds and/or for those substances with a high lipophilic to hydrophilic balance.

Also provided by the present invention is a method of treating a patient suffering from a disorder of the CNS arising from aberrant NMDA receptor behavior which comprises administering to the patient a therapeutically effective amount of a compound of the invention.

Further provided by the present invention is the use of a compound of the invention in the manufacture of a medicament for the treatment of a disorder of the CNS arising from aberrant NMDA receptor behavior.

Disorders of the CNS which may be treated according to the invention include epilepsy, pain-related disorders, narcotic-related disorders (e.g. narcotic tolerance) and disorders arising from neuronal cell death following ischaemia or stroke or head and/or spinal cord injury or HIV infection. Further disorders which may be treated according to the present invention include psychiatric disorders (such as schizophrenia) and neurodegenerative diseases such as Alzheimer's disease, Parkinson's disease and Huntington's disease.

The compounds of the invention are antagonists at NMDA receptor sites in the CNS and show greater potency when compared to compounds of the prior art. Furthermore, the claimed compounds also show greater selectivity for NMDA receptor subtypes, such as, for example, for NR2C or NR2D over NR2A or NR2B. The selectivity of the compounds provides therapeutic advantages over known NMDA antagonists since enhanced selectivity reduces unwanted side-effects. Adverse side-effects encountered with prior art compounds include memory loss, psychotomimetic effects and loss of motor co-ordination. The alleviation of any of these side-effects is clearly advantageous.

The compounds of the invention may also be used as research tools for the study of NMDA receptors. When used as research tools, the compounds of the invention may be detectably labelled, e.g., by the incorporation of one or more $^3H$ atoms (replacing $^1H$ atoms) into the compounds of the invention. Preferably, the radiolabelling is by substitution of one or more $^1H$ atoms (e.g., by $^3H$) on the phenanthrene ring. Alternatively, such detectable labels may include fluorophore conjugates, chemiluminescent conjugates, and the like.

The invention will now be illustrated by reference to the following non-limiting examples.

EXAMPLE 1

Preparation of Piperazine-2,3-Dicarboxylic Acid

Pyrazine-2,3-dicarboxylic acid (21.27 g, 0.127 mol) was dissolved in an aqueous solution of sodium hydroxide (10.12 g, 0.253 mol) to give disodium pyrazine-2,3-dicarboxylic acid. The aqueous solution of the acid was hydrogenated under 40 p.s.i of hydrogen in the presence of platinum (IV) oxide catalyst (0.5 g) for a period of 3 days. The reaction mixture was filtered and the solvent removed to give an oil. The oil was bound onto an ion exchange resin (Dowex-AG-50 H$^+$ form) column, and was eluted with water until the eluant had a pH of 5. The column was eluted with a 10% aqueous solution of pyridine, the ninhydrin active fractions were combined and the solvent removed in vacuo. The solid was purified by crystallisation to give the title compound (25.64 g, 95.6%).

EXAMPLE 2

Preparation of 2-Carboxyphenanthrene

Bromine (4.7 ml, 0.091 mol) was added to an ice-cold solution of sodium hydroxide (12.7 g, 0.318 mol) in water (70 ml) to form a basic solution of sodium hypobromite. The sodium hypobromite solution was added to a stirred solution of 2-acetylphenanthrene in dioxane (70 ml) at 60–65° C. for 15 min. Excess sodium hypobromite was removed by the addition of 10% solution of sodium metabisulphite (20 ml).

Water (300 ml) was added and approximately 100 ml of solvent was removed under reduced pressure. The reaction mixture was acidified with concentrated HCl. The precipitate formed was filtered and washed with water to give the title compound as a solid (4.01 g, 99.2%).

EXAMPLE 3

Preparation of (±)-cis-1-(Phenanthrene-2-ylcarbonyl)Piperazine-2,3-Dicarboxylic Acid (PPDA)

2-Carboxyphenanthrene (2 g, 0.009 mol) was suspended in dry benzene (50 ml) and heated under reflux in the presence of thionyl chloride (5 ml) for 5 hr. The solvent was removed and the corresponding acid chloride was used without further purification. Piperazine-2,3-dicarboxylic acid (0.508 g, 0.003 mol) was dissolved in a 0.991 M aqueous sodium hydroxide solution (9.4 ml, 0.009 mol), dioxane (10 ml) was added and the solution was cooled to 0° C. A solution of the acid chloride (0.84 g, 0.0035 mol) in dioxane (10 ml) was added to the reaction mixture. The reaction was warmed to room temperature and stirred for 2–3 hr. The reaction mixture was acidified to pH 2–3 with aqueous HCl. The solid was filtered, dissolved in dioxane/$H_2O$ (50:50) and bound to an ion exchange resin (Dowex-AG50 $H^+$ form) chromatography column. It was eluted with dioxane/$H_2O$ (50:50) until organic impurities are removed. The column was eluted with 10% aqueous pyridine and the ninhydrin fractions were combined. The solvent was removed and the solid was crystallised from $H_2O$ to give a white solid (0.128 g, 12%). m.p.=218.1–221.7 ° C. (dec.); $^1$H NMR (300 MHz, NaOD/ $D_2O$) 7.7–8.8 (m, 9H, Ar), 5.6 (d, 0.5H, C$\underline{H}$—$CO_2H$, $J_{AB}$=2.6Hz), 4.8 (d, 0.5H, C$\underline{H}$—$CO_2H$, $J_{AB}$=2.6Hz), 4.4 (d, 0.4H, C$\underline{H}$—$CO_2H$, $J_{AB}$=12.0Hz), 3.6 (d, 0.4H, C$\underline{H}$—$CO_2H$, $J_{AB}$=12.0Hz), 2.5–3.8 (m, 4H, N—C$\underline{H}_2$C$\underline{H}_2$—NH); Elemental analysis calculated for $C_{21}H_{18}N_2O_5$. $2.3H_2O$ C:60.07, H:5.44, N:6.67. Found C:60.06, H:5.38, N: 6.85. The cis-isomerism was confirmed by COSEY $^1$H NMR.

EXAMPLE 4

Preparation of 10-Bromophenanthrene-2-Carboxylic Acid (2)

Phenanthrene-2-carboxylic acid (1, 0.116 g, 0.5 mmol) was dissolved in acetic acid at 70° C. and then bromine (0.027 ml, 0.5 mmol) was added. The mixture was stirred at 70° C. overnight. The following day, bromine (0.027 ml, 0.5 mmol) was added and the mixture was refluxed for 6 h and then allowed to cool. The resulting precipitate was collected by filtration. $^1$H NMR (270 MHz, DMSO): 7.8 (m, 2H), 8.1 (d, 1H), 8.25 (d, 1H), 8.45 (s, 1H), 8.9 (s, 1H), 8.95 (m, 1H) and 9.05 (d, 1H).

EXAMPLE 5

Preparation of (±)-cis-1-(10-Bromophenanthrene-2-Carbonyl)Piperazine-2,3-Dicarboxylic Acid (5)

10-Bromophenanthrene-2-carboxylic acid (2, 0.663 g, 2.2 mmol) was added to benzene (50 ml) containing excess thionyl chloride and the mixture heated under reflux overnight. The following day, the mixture was evaporated under reduced pressure and the resulting acid chloride (3) used without further purification. (_)-Cis-piperazine-2,3-dicarboxylic acid (4, 0.46 g, 2.6 mmol) was added to 0.991 M aqueous sodium hydroxide (8 ml, 8 mmol) and dioxan (10 ml) and the mixture was cooled to 0° C. A solution of the crude acid chloride (3) in dry dioxan was then added and the mixture was stirred at 0° C. for 5 min and then at room temperature overnight. The following day, the reaction mixture was reduced to~ half the volume by evaporation under reduced pressure and was then acidified with 6 M aqueous hydrochloric acid. The resulting precipitate was collected by filtration, heated in dioxan (50–100 ml) and filtered. This procedure was then repeated twice. The resulting solid was added to water just below the boiling point and stirred in order to dissolve water soluble by-products. The insoluble material was collected by filtration, washed with dioxan and dried to give (±)-cis-1-(10-bromophenanthrene-2-carbonyl) piperazine-2,3-dicarboxylic acid (5) as a white solid. $^1$H NMR (270 MHz, $D_2O$/NaOD): 2.5–3.4 (m, 4H), 4.3 (d, 0.5 H), 5.5 (d, 0.5 H), 7.2–7.6 (m), 7.65–7.8 (m), 7.75 (s) 7.95–8.2 (m), 8.1 (s) and 8.25–8.5 (m).

EXAMPLE 6

Hemisected neonatal rat spinal cords (Evans and Watkins, European Journal of Pharmacology, 50: 123–129, 1978) were isolated and wire electrodes were placed under the exposed ventral roots. The preparation was superfused with standard Ringers (containing in mM: NaCl 118, $NaHCO_3$ 25, KCl 3, $CaCl_2$ 2.5, D-glucose 12 and gassed with 95% $O_2$/5% $CO_2$). To record agonist-induced responses, 0.1 $\mu$M tetrodotoxin was included to block synaptic transmission and associated depolarizations. Agonist (N-methyl-D-aspartate (NMDA)) was superfused for 60–120 seconds at a rate of 1 ml/minute. The relative positive potentials recorded by the distal (to spinal cord) wire electrode compared to the proximal electrode was taken as an indication of motor neuron cell body depolarization. Antagonism of agonist-induced responses was observed by co-application of the antagonist PPDA.

FIG. 1 shows the effect of PPDA on ionotropic receptors on motoneurones in the neonatal rat spinal cord. This figure is a graph of a Schild analysis of NMDA-induced depolarizations in the spinal cord showing that PPDA is a competitive antagonist with an affinity (Kd) of 247 nM. The DR is the dose ratio of agonist concentration in presence of antagonist that produces a comparable response when compared to treatment with the agonist alone. Thus, higher agonist concentrations are necessary (higher DR) to reverse the block of higher concentrations of PPDA indicating that the blockade is one of a competitive nature. PPDA is as potent as CPP-ene as an antagonist of NMDA-induced depolarizations in the spinal cord.

AMPA and kainate are protypical agonists which show selectivity for, and predominantly activate, the AMPA and kainate subtypes of glutamate receptors. In additional assays, PPDA was tested at a concentration of 5 $\mu$M (which is approximately 20 times the $K_d$ value for the antagonism of NMDA receptors) as an antagonist of AMPA (6 $\mu$M)-, kainate (50 $\mu$M)- and NMDA (50 $\mu$M)-induced depolarizations (approximate $EC_{50}$ concentrations used) on neonatal rat motoneurones. The results are shown below. Results:

88% antagonism of NMDA

15% antagonism of AMPA

21% antagonism of kainate

These results show that PPDA selectively binds the NMDA subtype of glutamate receptor.

PPDA (50 $\mu$M) also had no effect on depolarizations following administration of (1S,3R)-1-amino-1,3-cyclopentane dicarboxylic acid (ACPD; 30 $\mu$M). APCD is a Group I metabotropic glutamate (mGlu) receptor agonist.

The recited values were determined by using quantitative receptor autoradiography of [$^3$H]-glutamate labeled NMDA receptors in rat brain tissue sections. The data shows that PPDA is selective NMDA receptor antagonist having weaker antagonist activity on AMPA/kainate receptors and substantially no antagonist activity on group I mGlu receptors.

$\mu$M, PPDA inhibited 44.6±1.3% of 100 nM [$^3$H] 6-cyano-7-nitroquinoxaline-2,3-dione (CNQX) binding to native AMPA receptors and 9.3±6.7% of 25 nM [$^3$H]kainate (n=3).

The selectivity of PPDA for different NMDA receptor subtypes was investigated. The results are shown in Table 2.

TABLE 2

| $K_i$ values for recombinant NMDA receptors containing NR2 subunits A–D | | | | |
|---|---|---|---|---|
| | PPDA | PBPD | CPP-ene | D-AP5 |
| NR1/NR2A ($K_i$ ($\mu$M)) | 0.680.6 +/– 0.17 | 15.79 +/– 0.43 | 0.11 +/– 0.03 | 0.28 +/– 0.02 |
| NR1/NR2B ($K_i$ ($\mu$M)) | 0.35 +/– 0.02 | 5.01 +/– 0.25 | 0.14 +/– 0.04 | 0.46 +/– 0.14 |
| NR1/NR2C ($K_i$ ($\mu$M)) | 0.07 +/– 0.015 | 8.98 +/– 0.18 | 1.46 +/– 0.08 | 1.64 +/– 0.14 |
| NR1/NR2D ($K_i$ ($\mu$M)) | 0.11 +/– 0.03 | 4.29 +/– 0.11 | 1.84 +/– 0.74 | 3.71 +/– 0.67 |

The potency of PPDA for native NMDA receptors was also investigated in a Xenopus oocyte system. The results are shown in Table 1.

TABLE 1

| PPDAs Differentiate between Subclasses of NMDA Receptors in vitro in *Xenopus* oocytes. | |
|---|---|
| Native NMDA Receptor Potency | PPDA $K_i$ ($\mu$M) |
| Medial Striatum (NR2B) | 0.54 +/– 0.04 |
| Cerebellum (NR2A/NR2C) | 7.2 and 0.39 $\mu$M, respectively |
| Midline thalamus (NR2B/NR2D) | 0.31 +/– 0.03 |

EXAMPLE 7

PPDAs Differentiate Between Lonotropic Receptors in vitro in Xenopus Oocytes

RNA translation and transcription in Xenopus oocytes and electrophysiological recordings were performed as previously described (Monaghan D T, Larson H (1997) J Pharmacol Exp Ther 280:614 –620). Plasmids were linearized with NotI (NR1a), EcoRI (NR2A, NR2C, and NR2D), or SalI (NR2B) and transcribed in vitro using the mMessage mMachine RNA polymerase transcription kit (Ambion, Austin, Tex.). NR1 a was mixed 1:3 with NR2A, NR2B, NR2C, or NR2D RNA, and 2–50 ng of this mixture was injected into oocytes. Agonist-evoked responses were measured using a standard two-microelectrode voltage clamp (model OC-725B Oocyte Clamp; Warner Instruments, Hamden, Conn.) at a holding potential of –60 mV. Glutamate (10 $\mu$M) and glycine (10 $\mu$M) were applied until stable plateau responses were obtained; (±)-cis-1-(phenanthren-2-yl-carbonyl)-piperazine-2,3-dicarboxylic acid (PPDA) (0.1, 0.3, 1, 3, 10, or 30 $\mu$M) was then applied until steady-state blockade was obtained, followed by antagonist washout and full agonist responses. Current responses were captured and analyzed with AxoData (Axon Instruments, Foster City, Calif.) and GraphPad Prism (ISI Software, San Diego, Calif.) software. $K_i$ values were corrected for agonist affinity according to the Cheng-Prusoff equation. Data in Table 3 are expressed as mean $K_i$ ±SEM. PPDA was found to have little effect on native non-NMDA glutamate receptors. Autoradiography, performed as described by Monaghan D T in: Receptor autoradiography: principles and practice (Wharton J, Polak J M, eds), pp 171–193. New York: Oxford UP. (1993), showed that at 10

In Table 2, the $K_i$ values were obtained from NR2 subunits recombinantly expressed with NR1a subunits to form receptors in Xenopus oocytes. The $K_i$ values for D-AP5 and D-CPPene are from Buller A L, Monaghan D T (1997) Eur J Pharmacol 320:87–94 (mean±SEM; n=4–6); in the $K_i$ values for PPDA, n=3. Differences among the agents were expressed by normalization to PPDA [(2C+2D) $K_i$(2A+2B) $K_i^{nL\ PPDA}$] and obtained by dividing the ratios for each drug by the ratio for PPDA.

What is claimed is:
1. A compound of formula (I)

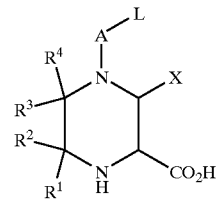

(I)

wherein: L is

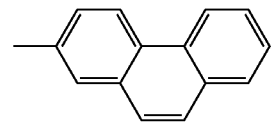

Optionally substituted by replacement of up to 9 of the hydrogen atoms on the phenanthrene ring system by up to 9 independently selected substituent groups;

A is $CH_2$, $SO_2$ or C=O;

X is $CO_2H$, $PO_2H_2$, $PO_2H_2$, $PO_2HR^5$, $PO_2HOR^5$, $SO_3H$, $SO_2H$, or tetrazole; and $R^1$, $R^2$, $R^3$, $R^4$ and $R^5$ are independently selected from H, alkyl, alkenyl, alkynyl, aryl and aralkyl;

or a pharmaceutically acceptable acid salt or base addition salt or an in vivo hydrolysable ester or amide thereof.

2. The compound of claim 1, wherein A is C=O.
3. The compound as claimed in claim 1, wherein X is $CO_2H$.
4. The compound as claimed in claim 1, wherein $R^1$, $R^2$, $R^3$, $R^4$ and, if present, $R^5$ are all H.
5. The compound as claimed in claim 1, wherein L is unsubstituted.

6. The compound as claimed in claim 1 wherein the groups X and —CO₂H are cis to each other.

7. The compound as claimed in claim 1 which is cis-1-(phenanthrene-2-carbonyl)piperazine-2,3-dicarboxylic acid.

8. The compound as claimed in claim 1 which is radio-labelled.

9. A pharmaceutical composition comprising a compound of claim 1 together with a pharmaceutically acceptable diluent or carrier.

10. A process for producing a compound of claim 1 which comprises the reaction of a compound of formula (II):

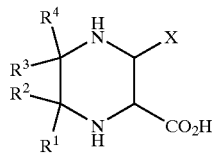

(II)

with a compound of formula L-A-M wherein: R¹, R², R³, R⁴, X, L and A are as defined in claim 1; and M is a leaving group.

11. The process as claimed in claim 10, wherein M is halo.

12. A method of treating a patient suffering from a disorder of the CNS arising from aberrant NMDA receptor behavior which comprises administering to the patient a therapeutically effective amount of a compound of claim 1.

13. The method as claimed in claim 12, wherein the disorder of the CNS is selected from the group consisting of epilepsy, pain-related disorders, narcotics-related disorders, disorders arising from neuronal cell death following ischaemia or stroke or head and/or spinal cord injury or HIV infection, psychiatric disorders, schizophrenia, neurodegenerative disorders, Alzheimer's disease, Parkinson's disease and Huntingdon's disease.

14. The compound according to claim 1, (±)-cis-1-(10-bromophenanthrene-2-carbonyl)piperazine-2,3-dicarboxylic acid.

15. The compound as claimed in claim 2, wherein X is CO₂H.

16. The compound as claimed in claim 15, wherein said substituent groups on the phenanthrene ring system may be the same or different and are selected from the group consisting of halo, cyano, hydroxy, alkoxy, alkyl, alkenyl, alkynyl, aryl and aralkyl wherein said alkyl, alkenyl, alkynyl, aryl and aralkyl groups may be optionally substituted with at least one group selected from halo, cyano, hydroxy, alkoxy, alkyl, alkenyl, alkynyl, aryl and aralkyl and said aryl moiety is optionally substituted on the ring by at least one of the same or different groups selected from halo, cyano, hydroxy, nitro, aikyl, alkenyl and alkynyl.

* * * * *